United States Patent
Suzuki et al.

(10) Patent No.: US 7,799,957 B2
(45) Date of Patent: Sep. 21, 2010

(54) PROCESS FOR PRODUCING PRODUCT OF HYDROGENOLYSIS OF POLYHYDRIC ALCOHOL

(75) Inventors: Nobuyoshi Suzuki, Wakayama (JP); Yohei Yoshikawa, Wakayama (JP); Masakatsu Takahashi, Wakayama (JP); Masazumi Tamura, Wakayama (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 12/227,025

(22) PCT Filed: Apr. 23, 2007

(86) PCT No.: PCT/JP2007/058713

§ 371 (c)(1), (2), (4) Date: Nov. 5, 2008

(87) PCT Pub. No.: WO2007/129560

PCT Pub. Date: Nov. 15, 2007

(65) Prior Publication Data

US 2009/0177018 A1 Jul. 9, 2009

(30) Foreign Application Priority Data

May 9, 2006 (JP) ............................. 2006-129850

(51) Int. Cl.
*C07C 29/132* (2006.01)
(52) U.S. Cl. ........................................... 568/861
(58) Field of Classification Search .................. 568/861
See application file for complete search history.

(56) References Cited

U.S. PATENT DOCUMENTS

| 4,642,394 A | 2/1987 | Che |
| 5,426,249 A | 6/1995 | Haas et al. |

FOREIGN PATENT DOCUMENTS

| JP | 6-192147 A | 7/1994 |
| JP | 2001-510816 A | 8/2001 |

OTHER PUBLICATIONS

J. Chaminand et al., Green Chemistry, 2004, vol. 6, pp. 359-361.
M. Schlaf et al., Angewandte Chemie, 2001, vol. 40, No. 20, pp. 3887-3890.

*Primary Examiner*—Elvis O Price
(74) *Attorney, Agent, or Firm*—Birch, Stewart, Kolasch & Birch, LLP

(57) ABSTRACT

The present invention relates to a process for producing hydrogenolysis products of polyhydric alcohols with a high selectivity as well as hydrogenolysis catalysts used in the hydrogenolysis reaction. The present invention provides a process for producing a hydrogenolysis product of a polyhydric alcohol which includes the step of reacting the polyhydric alcohol with hydrogen in the presence of a catalyst containing (A) a platinum-supporting heterogeneous catalyst component and (B) at least one catalyst component selected from the group consisting of tungsten components and molybdenum components, or in the presence of a catalyst containing a heterogeneous catalyst component formed by supporting (A') platinum and the above catalyst component (B), on a common carrier; as well as catalysts for hydrogenolysis of polyhydric alcohols.

10 Claims, No Drawings

PROCESS FOR PRODUCING PRODUCT OF HYDROGENOLYSIS OF POLYHYDRIC ALCOHOL

FIELD OF THE INVENTION

The present invention relates to a process for producing hydrogenolysis products of polyhydric alcohols with a high selectivity using a specific heterogeneous catalyst, as well as catalysts for hydrogenolysis of polyhydric alcohols used in the above process.

BACKGROUND OF THE INVENTION

The C3 alcohols are useful as various industrial raw materials, etc. Among these C3 alcohols, diols, in particular, 1,3-propanediol (hereinafter occasionally referred to merely as "1,3-PD"), have been noticed as raw materials of polyesters and polyurethanes. Therefore, it has been recently demanded to develop processes for producing the 1,3-PD in an efficient and inexpensive manner.

As the method for producing the 1,3-PD, there are conventionally known (1) a method in which ethylene oxide is hydroformylated to synthesize 3-hydroxypropanal which is then hydrogenated to produce the 1,3-PD, and (2) a method in which acrolein is hydrogenated to synthesize 3-hydroxypropanal which is then hydrogenated to produce the 1,3-PD.

However, in these conventional methods, the 1,3-PD must be produced by the two-step reactions and via 3-hydroxypropanal as a thermally unstable intermediate product, resulting in high production costs owing to deterioration in yield of the 1,3-PD. For this reason, it has been further demanded to develop a process for producing the 1,3-PD with low costs.

On the other hand, there are also known methods for hydrogenolysis of polyhydric alcohols such as, for example, glycerol, in which the glycerol is converted into 1,2-propanediol (hereinafter occasionally referred to merely as "1,2-PD") and 1,3-PD in a one-step reaction. For example, as the hydrogenolysis methods, there are disclosed a method using a homogeneous catalyst containing tungsten and a metal component belonging to Group VIII of the Periodic Table (short-form Periodic Table) (for example, refer to Patent Document 1), and a method using a homogeneous catalyst composed of a platinum-group metal complex and an anion source (for example, refer to Patent Document 2).

Patent Document 1: U.S. Pat. No. 4,642,394
Patent Document 2: JP 2001-510816A

SUMMARY OF THE INVENTION

The present invention relates to:

(1) A process for producing a hydrogenolysis product of a polyhydric alcohol, which includes the step of reacting the polyhydric alcohol with hydrogen in the presence of a catalyst containing (A) a platinum-supporting heterogeneous catalyst component and (B) at least one catalyst component selected from the group consisting of tungsten components and molybdenum components;

(2) a process for producing a hydrogenolysis product of a polyhydric alcohol, which includes the step of reacting the polyhydric alcohol with hydrogen in the presence of a catalyst containing a heterogeneous catalyst component formed by supporting (A') platinum and (B) at least one catalyst component selected from the group consisting of tungsten components and molybdenum components, on a common carrier;

(3) a catalyst for hydrogenolysis of polyhydric alcohols which includes (A) a platinum-supporting heterogeneous catalyst component and (B) at least one catalyst component selected from the group consisting of tungsten components and molybdenum components; and (4) a catalyst for hydrogenolysis of polyhydric alcohols which includes a heterogeneous catalyst component formed by supporting (A') platinum and (B) at least one catalyst component selected from the group consisting of tungsten components and molybdenum components, on a common carrier.

DETAILED DESCRIPTION OF THE INVENTION

The conventionally known methods for producing hydrogenolysis products of polyhydric alcohols as described in the above Patent Documents tend to suffer from problems such as low selectivity to most useful 1,3-PD and difficulty in industrially practicing them owing to the homogeneous catalysts used therein.

Thus, the present invention relates to a process for producing a hydrogenolysis product of a polyhydric alcohol with a high selectivity using a specific heterogeneous catalyst, as well as a catalyst for hydrogenolysis of polyhydric alcohols which is usable in the process.

The present inventors have found that the hydrogenolysis product is produced from the polyhydric alcohol with a high selectivity by using, as a hydrogenolysis catalyst for the polyhydric alcohol, a catalyst containing a platinum-supporting heterogeneous catalyst component and at least one catalyst component selected from the group consisting of tungsten components and molybdenum components, or a catalyst containing a heterogeneous catalyst component formed by supporting platinum and the at least one catalyst component selected from the group consisting of tungsten components and molybdenum components, on a common carrier.

In the process for producing a hydrogenolysis product of a polyhydric alcohol according to the present invention, the polyhydric alcohol and hydrogen are heated in the presence of the hydrogenolysis catalyst to hydrogenolyze the polyhydric alcohol. In the followings, the production process of the present invention is more specifically explained.

Examples of the polyhydric alcohol to be hydrogenolyzed according to the present invention include aliphatic or alicyclic polyhydric alcohols having 2 to 60 carbon atoms. Specific examples of the polyhydric alcohol include ethylene glycol, diethylene glycol, triethylene glycol, polyethylene glycol, various propanediols, various dipropanediols, various tripropanediols, various butanediols, various dibutanediols, various pentanediols, various pentanetriols, various hexanediols, various hexanetriols, glycerol, diglycerol, triglycerol, polyglycerol, various cyclohexanediols, various cyclohexanetriols, pentaerythritol, trimethylolpropane, and sugar alcohols such as sorbitol and mannitol. Among these polyhydric alcohols, glycerol is especially preferred from the industrial viewpoint.

The hydrogenolysis product of the polyhydric alcohol as used herein means a compound obtained by reacting the polyhydric alcohol with hydrogen to decompose hydroxyl groups thereof to such an extent that at least one of the hydroxyl groups remains undecomposed. For example, the hydrogenolysis product of glycerol (number of hydroxyl groups in molecule: 3) includes C3 diol (number of hydroxyl groups in molecule: 2) and C3 monool (number of hydroxyl groups in molecule: 1).

The hydrogenolysis catalyst used in the above process is a catalyst containing (A) a platinum-supporting heterogeneous catalyst component and (B) at least one catalyst component selected from the group consisting of tungsten components and molybdenum components (hereinafter occasionally refer to merely as the "hydrogenolysis catalyst I"), or a catalyst containing a heterogeneous catalyst component formed by supporting (A') platinum and (B) the at least one catalyst component selected from the group consisting of tungsten components and molybdenum components, on a common carrier (hereinafter occasionally refer to merely as the "hydrogenolysis catalyst II").

The carrier of the platinum-supporting heterogeneous catalyst component (A) in the hydrogenolysis catalyst I is not particularly limited. Examples of the carrier usable in the catalyst include those carriers as described in "Studies in Surface and Catalysis", 1-25, vol. 51, 1989. Among these carrier, especially preferred are alumina and carbons (such as activated carbon). In addition to these carriers, tungsten oxide and molybdenum oxide may also be used as the carrier. In this case, the tungsten oxide or molybdenum oxide can exhibit a combined function as the below-mentioned catalyst component (B). The amount of platinum supported on the carrier is usually from about 0.1 to about 30% by mass and preferably from 1 to 20% by mass on the basis of a total amount of the carrier and platinum supported thereon from the viewpoint of a good catalytic activity.

The amount of the platinum-supporting heterogeneous catalyst component used as the component (A) may be appropriately determined depending upon kinds of the polyhydric alcohols to be hydrogenolyzed, and is preferably 0.0001 g or more, more preferably from 0.001 to 0.5 g and still more preferably from 0.01 to 0.2 g in terms of platinum element on the basis of 1 g of the polyhydric alcohol from the viewpoint of good conversion rate and selectivity.

The tungsten component as the catalyst component (B) used together with the above component (A) may be composed of tungsten (W) as a 0-valent metal itself and/or various inorganic compounds, organic compounds or complex compounds of tungsten. Specific examples of the tungsten component include tungstic acid ($H_2WO_4$), salts of tungstic acid, tungsten oxide, tungsten hexacarbonyl and ammonium paratungstate.

The tungstic acid or salts thereof used in the present invention may include tungstic acid, and alkali metal salts or alkali earth metal salts of tungstic acid. Among these tungsten components, especially preferred is tungstic acid. The tungstic acid may be present in the form of ortho-tungstic acid, meta-tungstic acid or para-tungstic acid. Any of these tungstic acids may be used in the present invention. In general, the ortho-tungstic acid ($H_2WO_4$) is suitably used.

The molybdenum component as the catalyst component (B) may be composed of molybdenum (Mo) as a 0-valent metal itself and/or various inorganic compounds, organic compounds or complex compounds of molybdenum. Specific examples of the molybdenum component include molybdenum hexacarbonyl, ammonium molybdate, molybdenum acetate and molybdenum oxide.

The heteropolyacids or salts thereof used as the catalyst component (B) may include heteropolyacids, and alkali metal salts or alkali earth metal salts of the heteropolyacids. Among these compounds, especially preferred are the heteropolyacids.

The heteropolyacids suitably used in the present invention contain at least one element selected from molybdenum (Mo) and tungsten (W). Among these heteropolyacids, preferred are those containing at least one element selected from the group consisting of Mo and W and at least one element selected from the group consisting of Si and P.

Specific examples of the heteropolyacids include phosphotungstic acid ($H_3PW_{12}O_{40}$), silicotungstic acid ($H_3SiW_{12}O_{40}$) and phosphomolybdic acid ($H_3PMo_{12}O_{40}$).

These catalyst components (B) used together with the catalyst component (A) in the hydrogenolysis catalyst I may be used alone or in combination of any two or more thereof. The amount of the catalyst component (B) used may be appropriately determined depending upon the polyhydric alcohol to be hydrogenolyzed, etc., and is preferably 0.0001 g or more, more preferably from 0.001 to 5 g and still more preferably from 0.01 to 5 g on the basis of 1 g of the polyhydric alcohol from the viewpoint of good conversion rate and selectivity.

The hydrogenolysis catalyst I may be produced by mixing the catalyst component (A) with the catalyst component (B).

On the other hand, the hydrogenolysis catalyst II is a catalyst containing a heterogeneous catalyst component formed by supporting platinum as the catalyst component (A') and the above catalyst component (B), on a common carrier. Examples of the common carrier include those carriers exemplified for the catalyst component (A) of the hydrogenolysis catalyst I.

In the hydrogenolysis catalyst II, the mass ratio of platinum as the catalyst component (A') to the catalyst component (B) which are supported on the common carrier is usually from about 100:1 to about 1:100, preferably from 10:1 to 1:20 and more preferably from 5:1 to 1:10 in terms of the metal elements.

The hydrogenolysis catalyst II may be produced by supporting the catalyst component (A') and the catalyst component (B) on the carrier by an ordinary known method such as precipitation, ion exchange, evaporation to dryness, spray drying and kneading, though not particularly limited to these methods.

Meanwhile, when tungsten oxide or molybdenum oxide is used as the carrier, these oxide may exhibit a combined function as the catalyst component (B).

In the process for producing the hydrogenolysis product of the polyhydric alcohol according to the present invention in which the polyhydric alcohol is reacted with hydrogen in the presence of the specific catalyst, it is preferable to well control the temperature in the reaction. The temperature control may be conducted by heating or by using a heat of the reaction. The hydrogen used in the reaction may be either a hydrogen gas only or a dilute gas obtained by diluting hydrogen with an inert gas such as nitrogen and helium.

The process for producing the hydrogenolysis product of the polyhydric alcohol according to the present invention is preferably carried out without using any reaction solvent from the viewpoint of simplified production procedure. However, the hydrogenolysis of the polyhydric alcohol may also be conducted in the presence of the reaction solvent.

The reaction solvent is preferably a protonic solvent. As the reaction solvent, there may be used, for example, at least one solvent selected from the group consisting of water, methanol, ethanol, 1-propanol, 2-propanol, n-butanol, isobutanol, 1,2-propanediol, 1,3-propanediol and ethylene glycol. Among these reaction solvents, preferred are those containing water from the viewpoint of a good reaction efficiency.

The reaction solvent is used in such an amount that the content of the polyhydric alcohol in the resultant solution is preferably 1% by mass or more and more preferably 10% by mass or more.

In the process of the present invention, a hydrogen gas as the raw material may be used as such or in the form of a dilute gas prepared by diluting hydrogen with an inert gas such as nitrogen, argon and helium.

The reaction conditions are not particularly limited, and may be appropriately determined according to kinds of the polyhydric alcohol and catalyst used in the reaction. In general, the hydrogen pressure is preferably 30 MPa or less and more preferably from 0.1 to 10 MPa as measured at room temperature. The reaction temperature of 80° C. or higher is usually sufficient to carry out the hydrogenolysis. From the viewpoints of a good conversion rate of the polyhydric alcohol by hydrogenolysis as well as a good selectivity to the aimed hydrogenolysis product, the reaction temperature is preferably in the range of from 120 to 240° C.

The hydrogenolysis reaction may be conducted by either a batch method or a continuous method. The reaction apparatus is not particularly limited, and there may be used apparatuses capable of being pressurized such as an autoclave, fixed-bed flow type apparatuses, etc.

In the process for producing the hydrogenolysis product of the polyhydric alcohol according to the present invention, glycerol is preferably used as the polyhydric alcohol. When using glycerol as the polyhydric alcohol, a mixture composed of 1,3-propanediol, 1,2-propanediol, 1-propanol, 2-propanol, etc., can be produced as the hydrogenolysis product.

Also, the present invention provides a catalyst for hydrogenolysis of polyhydric alcohols which contains (A) a platinum-supporting heterogeneous catalyst component and (B) at least one catalyst component selected from the group consisting of tungsten components and molybdenum components; and a catalyst for hydrogenolysis of polyhydric alcohols which contains a heterogeneous catalyst component formed by supporting (A') platinum and (B) the at least one catalyst component selected from the group consisting of tungsten components and molybdenum components, on a common carrier.

EXAMPLES

Example 1

A 500 mL autoclave made of titanium and equipped with a stirrer was charged with 4 g of 5% by mass Pt/C, 6 g of $H_2WO_4$, 12 g of glycerol and 120 g of water, and an interior of the autoclave was replaced with hydrogen. Thereafter, hydrogen was introduced into the autoclave until reacting 3 MPa, and then the contents in the autoclave were heated and reacted with each other at 160° C. for 3 h. As a result, it was confirmed that the conversion rate of glycerol was 9%, the selectivity to the respective reaction products was 41 mol % for 1,3-PD, 17 mol % for 1,2-PD, 24 mol % for 1-propanol and 18 mol % for 2-propanol, and none of byproducts such as hydrocarbon gases were produced. The results are shown in Table 1.

Examples 2 to 8 and Comparative Examples 1 to 8

The same procedure as in Example 1 was repeated except that the reaction was conducted under the conditions shown in Tables 1 and 2. The results are shown in Tables 1 and 2.

Example 9

Production of Catalyst

A 2% by mass ammonium para-tungstate aqueous solution in an amount of 21 mL was applied onto 6.0 g of a commercially available 5% by mass Pt/$Al_2O_3$ and supported thereon by evaporation to dryness, and then dried at 120° C. for 3 h. Further, the resulting product was calcined at 500° C. for 2 h in an air flow. The thus obtained catalyst was composed of 5% by mass of Pt and 5% by mass of W which were supported on alumina ($Al_2O_3$).

(Reaction)

A 500 mL autoclave made of titanium and equipped with a stirrer was charged with 4 g of the above prepared catalyst, 12 g of glycerol and 120 g of water, and an interior of the autoclave was replaced with hydrogen. Thereafter, hydrogen was introduced into the autoclave until reacting 3 MPa, and then the contents in the autoclave were heated and reacted with each other at 160° C. for 3 h. As a result, it was confirmed that the conversion rate of glycerol was 20%, and the selectivity to the respective reaction products was 67 mol % for 1,3-PD, 4 mol % for 1,2-PD, 18 mol % for 1-propanol and 10 mol % for 2-propanol. The results are shown in Table 3.

Examples 10 to 12

Using a commercially available Pt/$Al_2O_3$, tungsten was supported thereon in an amount shown in Table 3 in the same manner as in Example 9, and then the reaction was conducted under the conditions shown in Table 1 in the same manner as in Example 9. The results are shown in Table 3.

Example 13

A 10% by mass chloroplatinic acid aqueous solution in an amount of 6.3 mL was applied onto 6.0 g of a commercially available $WO_3$ and supported thereon by evaporation to dryness, and then dried at 120° C. for 3 h. Further, the resulting product was calcined at 500° C. for 2 h in an air flow. Using 4 g of the thus obtained catalyst, the reaction was conducted in the same manner as in Example 9. The results are shown in Table 3.

Comparative Examples 9 to 11

Using a commercially available Pd/$Al_2O_3$, Ru/$Al_2O_3$ or Rh/$Al_2O_3$, the catalyst was produced in the same manner as in Example 9, and the reaction was conducted under the conditions shown in Table 2 in the same manner as in Example 9. The results are shown in Table 4.

Meanwhile, after completion of the reaction, the obtained reaction solution was subjected to filtration and then analyzed by $^1$H-NMR for solution using the following apparatus to conduct a quantitative determination of the reaction product. In addition, the resultant gas component was collected in a gas bag and then analyzed by the following two kinds of gas chromatographic methods depending upon kinds of gases collected to conduct a quantitative determination of the reaction product.

1) $^1$H-NMR for Solution

Apparatus used: "Mercury 400" available from Varian Inc.; internal standard substance: sodium trimethylsilylpropionate 2) Gas Chromatography for Lower Hydrocarbon Gases Column: "Porapak Q"; 2.1 m×3.2 mmφ; 80-100 mesh; detector: FID; injection temperature: 200° C.; detector temperature: 200° C.; flow rate of He: 6 mL/min 3) Gas Chromatography for CO, $CO_2$ Gases Column: "Molecular Sieve 5A"; detector: FID (with a metanizer fitted between the column and the detector); injection temperature: 80° C.; detector temperature: 80° C.; flow rate of He: 60 mL/min

TABLE 1-1

| | Examples | | | |
|---|---|---|---|---|
| | 1 | 2 | 3 | 4 |
| Reaction conditions | | | | |
| Catalyst | 5% Pt/C $H_2WO_4$ | 5% Pt/C $H_3PW_{12}O_{40} \cdot nH_2O$ | 5% Pt/C $H_3SiW_{12}O_{40} \cdot nH_2O$ | 5% Pt/C $H_3PMo_{12}O_{40} \cdot nH_2O$ |
| Hydrogen pressure [at room temperature] (MPa) | 3 | 3 | 3 | 3 |
| Reaction temperature (° C.) | 160 | 160 | 160 | 160 |
| Reaction solvent | Water | Water | Water | Water |
| Reaction results | | | | |
| Conversion rate of glycerol (%) | 9 | 10 | 9 | 8 |
| Selectivity (mol %) | | | | |
| 1,3-Propanediol | 41 | 46 | 43 | 45 |
| 1,2-Propanediol | 17 | 10 | 16 | 26 |
| 1-Propanol | 24 | 34 | 29 | 18 |
| 2-Propanol | 18 | 5 | 10 | 8 |
| Ethylene glycol | 0 | 0 | 0 | 0 |
| Other and unknown substances | 0 | 5 | 2 | 3 |

(Note)
5% Pt/C: 5% by mass Pt/C

TABLE 1-2

| | Examples | | | |
|---|---|---|---|---|
| | 5 | 6 | 7 | 8 |
| Reaction conditions | | | | |
| Catalyst | 5% Pt/C $H_2WO_4$ | 5% Pt/C $H_2WO_4$ | 5% Pt/C $H_2WO_4$ | 5% Pt/C $H_2WO_4$ |
| Hydrogen pressure [at room temperature] (MPa) | 5.5 | 3 | 3 | 3 |
| Reaction temperature (° C.) | 160 | 180 | 200 | 160 |
| Reaction solvent | Water | Water | Water | Glycerol |
| Reaction results | | | | |
| Conversion rate of glycerol (%) | 2 | 17 | 22 | 1 |
| Selectivity (mol %) | | | | |
| 1,3-Propanediol | 45 | 42 | 41 | 39 |
| 1,2-Propanediol | 10 | 15 | 9 | 27 |
| 1-Propanol | 25 | 29 | 29 | 22 |
| 2-Propanol | 10 | 7 | 8 | 4 |
| Ethylene glycol | 0 | 0 | 0 | 3 |
| Other and unknown substances | 10 | 7 | 13 | 5 |

(Note)
5% Pt/C: 5% by mass Pt/C

TABLE 2-1

| | Comparative Examples | | | |
|---|---|---|---|---|
| | 1 | 2 | 3 | 4 |
| Reaction conditions | | | | |
| Catalyst | 5% Pt/C — | — $H_2WO_4$ | 5% Pt/C TfOH | 5% Pt/C $CH_3SO_3H$ |
| Hydrogen pressure [at room temperature] (MPa) | 3 | 3 | 3 | 3 |
| Reaction temperature (° C.) | 160 | 160 | 160 | 160 |
| Reaction solvent | Water | Water | Water | Water |
| Reaction results | | | | |
| Conversion rate of glycerol (%) | 0 | 1 | 1 | 0 |
| Selectivity (mol %) | | | | |
| 1,3-Propanediol | No reaction products | 0 | 7 | No reaction products |
| 1,2-Propanediol | | 0 | 0 | |
| 1-Propanol | | 0 | 20 | |
| 2-Propanol | | 0 | 0 | |
| Ethylene glycol | | 0 | 0 | |
| Other and unknown substances | | 100 | 73 | |

(Note)
5% Pt/C: 5% by mass Pt/C
TfOH: Trifluoromethanesulfonic acid

TABLE 2-2

| | Comparative Examples | | | |
|---|---|---|---|---|
| | 5 | 6 | 7 | 8 |
| Reaction conditions | | | | |
| Catalyst | 5% Pt/C $H_3PO_4$ | 5% Pd/C $H_2WO_4$ | 5% Rh/C $H_2WO_4$ | 5% Ru/C $H_2WO_4$ |
| Hydrogen pressure [at room temperature] (MPa) | 3 | 3 | 3 | 3 |
| Reaction temperature (° C.) | 160 | 160 | 160 | 160 |

TABLE 2-2-continued

|  | Comparative Examples | | | |
| --- | --- | --- | --- | --- |
|  | 5 | 6 | 7 | 8 |
| Reaction solvent | Water | Water | Water | Water |
| Reaction results |  |  |  |  |
| Conversion rate of glycerol (%) | 0 | 0 | 7 | 3 |
| Selectivity (mol %) |  |  |  |  |
| 1,3-Propanediol | No reaction products | No reaction products | 18 | 0 |
| 1,2-Propanediol |  |  | 49 | 46 |
| 1-Propanol |  |  | 17 | 11 |
| 2-Propanol |  |  | 6 | 0 |
| Ethylene glycol |  |  | 0 | 0 |
| Other and unknown substances |  |  | 10 | 43 |

(Note)
5% Pt/C: 5% by mass Pt/C
5% Pd/C: 5% by mass Pd/C
5% Rh/C: 5% by mass Rh/C
5% Ru/C: 5% by mass Ru/C

TABLE 3

|  | Examples | | | | |
| --- | --- | --- | --- | --- | --- |
|  | 9 | 10 | 11 | 12 | 13 |
| Reaction conditions |  |  |  |  |  |
| Catalyst | Pt—W/Al$_2$O$_3$ (Pt5%, W5%) | Pt—W/Al$_2$O$_3$ (Pt5%, W5%) | Pt—W/Al$_2$O$_3$ (Pt5%, W30%) | Pt—W/Al$_2$O$_3$ (Pt10%, W5%) | Pt/WO$_3$ (Pt5%) |
| Hydrogen pressure [at room temperature] (MPa) | 3 | 5.5 | 3 | 3 | 3 |
| Reaction temperature (° C.) | 160 | 160 | 160 | 160 | 160 |
| Reaction solvent | Water | Water | Water | Water | Water |
| Conversion rate of glycerol (%) | 20 | 23 | 2 | 11 | 4 |
| Reaction results |  |  |  |  |  |
| Selectivity (mol %) |  |  |  |  |  |
| 1,3-Propanediol | 67 | 67 | 53 | 65 | 66 |
| 1,2-Propanediol | 4 | 5 | 5 | 5 | 10 |
| 1-Propanol | 18 | 16 | 27 | 15 | 9 |
| 2-Propanol | 10 | 11 | 8 | 12 | 7 |
| Other and unknown substances | 1 | 1 | 7 | 3 | 8 |

(Note)
Pt5%, W5%: 5% by mass Pt, 5% by mass W
Pt5%, W30%: 5% by mass Pt, 30% by mass W
Pt10%, W5%: 10% by mass Pt, 5% by mass W
Pt5%: 5% by mass Pt

TABLE 4

|  | Comparative Examples | | |
| --- | --- | --- | --- |
|  | 9 | 10 | 11 |
| Reaction conditions |  |  |  |
| Catalyst | Pd—W/Al$_2$O$_3$ (Pd5%, W5%) | Ru—W/Al$_2$O$_3$ (Ru5%, W5%) | Rh—W/Al$_2$O$_3$ (Rh5%, W5%) |
| Hydrogen pressure [at room temperature] (MPa) | 3 | 3 | 3 |
| Reaction temperature (° C.) | 160 | 160 | 160 |
| Reaction solvent | Water | Water | Water |
| Conversion rate of glycerol (%) | 0 | 3 | 1 |
| Reaction results |  |  |  |
| Selectivity (mol %) |  |  |  |
| 1,3-Propanediol | No reaction products | 0 | 3 |
| 1,2-Propanediol |  | 20 | 61 |
| 1-Propanol |  | 11 | 25 |
| 2-Propanol |  | 3 | 3 |
| Other and unknown substances |  | 66 | 8 |

(Note)
Pd5%, W5%: 5% by mass Pd, 5% by mass W
Ru5%, W5%: 5% by mass Ru, 5% by mass W
Rh5%, W5%: 5% by mass Rh, 5% by mass W From the results of the Examples shown in Tables 1 and 3 and the results of the Comparative Examples shown in Tables 2 and 4, it was confirmed that in the process for producing the hydrogenolysis products of polyhydric alcohols by using the specific catalyst according to the present invention, the hydrogenolysis products can be produced from the polyhydric alcohols, in particular, 1,3-propanediol can be produced from glycerol, with a high selectivity.

INDUSTRIAL APPLICABILITY

In the process for producing a hydrogenolysis product of a polyhydric alcohol according to the present invention, the hydrogenolysis product can be produced from the polyhydric alcohol, in particular, 1,3-propanediol can be produced from glycerol, with a high selectivity. Therefore, the process of the present invention can be suitably utilized for production of these hydrogenolysis products of polyhydric alcohols.

Also, the catalysts for hydrogenolysis of polyhydric alcohols according to the present invention can be effectively used, in particular, as a catalyst for producing 1,3-propanediol from glycerol with a high selectivity.

The invention claimed is:

1. A process for producing 1,3-propanediol, comprising the step of reacting glycerol with hydrogen in the presence of a heterogeneous catalyst containing (A) a platinum-supporting heterogeneous catalyst component and (B) at least one catalyst component selected from the group consisting of tungsten components and molybdenum components.

2. A process for producing 1,3-propanediol, comprising the step of reacting glycerol with hydrogen in the presence of a heterogeneous catalyst containing a heterogeneous catalyst component formed by supporting (A') platinum and (B) at least one catalyst component selected from the group consisting of tungsten components and molybdenum components, on a common carrier.

3. The process according to claim 1 or 2, wherein the catalyst component (B) is the tungsten component.

4. The process according to claim 1, wherein the catalyst component (B) contains at least one catalyst component selected from the group consisting of tungstic acid, salts of tungstic acid, heteropolyacids and salts of the heteropolyacids.

5. The process according to claim 1, wherein the catalyst component (B) is tungstic acid.

6. The process according to claim 4, wherein the catalyst component (B) is the heteropolyacid.

7. The process according to claim 1, wherein the reaction is conducted using a protonic solvent as a reaction solvent.

8. The process according to claim 7, wherein the protonic solvent contains water.

9. The process according to claim 1, wherein after the glycerol is reacted with hydrogen, 1,3-propanediol is present in a higher mol % than any other reaction product.

10. The process according to claim 2, wherein after the glycerol is reacted with hydrogen, 1,3-propanediol is present in a higher mol % than any other reaction product.

* * * * *